(12) United States Patent
Kondo et al.

(10) Patent No.: US 6,814,853 B2
(45) Date of Patent: Nov. 9, 2004

(54) WATER TREATING METHOD, WATER TREATING APPARATUS, AND HYDROPONIC SYSTEM USING THE SAME

(75) Inventors: Yasuhito Kondo, Ora-gun (JP); Yasuhito Shimizu, Ora-gun (JP); Masahiro Iseki, Ota (JP)

(73) Assignee: Sanyo Electric Co., Ltd., Moriguchi (JP)

( * ) Notice: Subject to any disclaimer, the term of this patent is extended or adjusted under 35 U.S.C. 154(b) by 318 days.

(21) Appl. No.: 10/048,455

(22) PCT Filed: Jun. 25, 2001

(86) PCT No.: PCT/JP01/05386
§ 371 (c)(1),
(2), (4) Date: Jul. 2, 2002

(87) PCT Pub. No.: WO02/00554
PCT Pub. Date: Jan. 3, 2002

(65) Prior Publication Data
US 2002/0170830 A1 Nov. 21, 2002

(51) Int. Cl.⁷ .............................................. C02F 1/461
(52) U.S. Cl. ....................... 205/701; 205/742; 205/743; 204/230.02; 204/275.1
(58) Field of Search ................................ 205/701, 742, 205/743; 204/230.02, 275.1; 210/601; 47/62 R

(56) References Cited
U.S. PATENT DOCUMENTS
5,614,078 A * 3/1997 Lubin et al. ................. 205/743
5,770,037 A 6/1998 Goto et al.

FOREIGN PATENT DOCUMENTS
JP 4-4822 1/1992
JP 9-234459 9/1997
JP 10-180259 7/1998

* cited by examiner

Primary Examiner—Arun S. Phasge
(74) Attorney, Agent, or Firm—Armstrong, Kratz, Quintos, Hanson & Brooks, LLP

(57) ABSTRACT

There is provided a method for water treatment, capable of greatly improving the effect of removing microbes contained in water for eating and drinking, or discharged water. This water treatment method comprises: a first treatment step of dipping a pair of electrodes and a conductor capable of collecting at least microbes in a running channel of water to be treated, and applying a positive potential to the conductor and applying negative potentials to the electrodes to adsorb the microbes on the conductor; a second treatment step of stopping the flow of the water to be treated after an end of the first treatment step, and increasing the potentials applied to the conductor and the electrodes to start the electrolysis of the water to be treated while the polarities of the potentials applied to the conductor and the electrodes are maintained intact in the presence of the water to be treated; and a third treatment step of stopping the application of the potential to the conductor after an end of the second treatment step, and applying a positive potential to one of the pair of electrodes and applying a negative potential to the other of the electrodes in the presence of the water to be treated.

11 Claims, 6 Drawing Sheets

WATER TREATING METHOD, WATER TREATING APPARATUS, AND HYDROPONIC SYSTEM USING THE SAME

BACKGROUND OF THE INVENTION

1. Field of the Invention

The present invention relates to a method and an apparatus for sterilizing water for eating and drinking, waste water discharged from a hydroponic system/fish hatchery, and the like.

2. Description of the Related Art

To remove microbes such as bacteria, mold and protozoa contained in water for eating and drinking such as tap water stored in, for example, a reservoir, a method has conventionally been employed which cleans up water by disposing a porous filter material capable of collecting the microbes in a running water channel, and securely capturing the microbes in the filter material.

In another method that has been employed in addition to the above method, electrodes are inserted into water for eating and drinking to perform electrolysis, whereby chlorine or ozone is generated, and by its sterilizing function, the microbes contained in water for eating and drinking are killed.

On the other hand, in the hydroponic system, crops planted in a cultivation bed have been properly grown by circulating a nutrient liquid prepared by dissolving fertilizer and manure in water at a rate suitable for crop cultivation to the cultivation bed. However, the interior of the cultivation bet to which the nutrient liquid has been circulated is an environment suitable for the propagation of pathogenic fungi such as fusarium fungi (a kind of mold). If the propagation of fusarium fungi occurs in the cultivation bed, crop roots are damaged, which kills the crops. Therefore, a device has been employed which is constructed to sterilize pathogenic fungi contained in the nutrient liquid by heating the nutrient liquid with a heater, or by ultraviolet rays or ozone contained in a light-transmissive jacket in the circulation channel of the nutrient liquid.

The above filter material receives and collects the microbes in fine holes formed on its surface. Accordingly, the microbes cannot securely be captured unless the microbes clash on the surface of the filter material or pass through its vicinity. Consequently, a limitation has been placed on the effect of securely capturing the microbes.

Since the microbes are securely captured in such a filter material as described above, a saturation state is reached in sooner or later to discharge the microbes into the running water channel. Accordingly, it can be contrived that the securely captured microbes are killed by heating the filter material, but some microbes have resistance to heat, and hence, to assure the effect of sterilization, the filter material must be heated to a relatively high temperature.

In addition, the nutrient liquid has been heated to sterilize the pathogenic fungi propagated in the cultivation bed in the hydroponic system, but since the plants are killed if the heated nutrient liquid is directly used as it is, a cooling device is necessary to cool the heated nutrient liquid. Consequently, there has been a problem that a large amount of energy must be used to heat and cool the nutrient liquid. Furthermore, when the pathogenic fungi contained in the nutrient liquid is sterilized by using ultraviolet rays or ozone, there has been another problem that the concentrations of iron and manganese contained in the nutrient liquid decrease.

The present invention has been developed to solve the foregoing conventional technical problems, and objects of the present invention are to provide a method and an apparatus for water treatment which can greatly improve the effect of removing microbes contained in water for eating and drinking or waste water, and a hydroponic system using the same.

SUMMARY OF THE INVENTION

According to a first aspect of the present invention, there is provided a method for water treatment comprising a first treatment step of dipping a pair of electrodes and a conductor capable of collecting at least microbes in a running channel of water to be treated, and applying a positive potential to the conductor and applying negative potentials to the electrodes to adsorb the microbes on the conductor; a second treatment step of stopping the flow of the water to be treated after an end of the first treatment step, and increasing the potentials applied to the conductor and the electrodes to start the electrolysis of the water to be treated while the polarities of the potentials applied to the conductor and the electrodes are maintained intact in the presence of the water to be treated; and a third treatment step of stopping the application of the potential to the conductor after an end of the second treatment step, and applying a positive potential to one of the pair of electrodes and applying a negative potential to the other of the electrodes in the presence of the water to be treated.

According to a second aspect of the present invention, there is provided a method for water treatment comprising a first treatment step of dipping a pair of electrodes and a conductor capable of collecting at least microbes in a running channel of water to be treated, and applying a positive potential to the conductor and applying negative potentials to the electrodes to adsorb the microbes on the conductor; a second treatment step of stopping the flow of the water to be treated after an end of the first treatment step, reversing the polarities of the potentials applied to the conductor and the electrodes in the presence of the water to be treated, and increasing the potentials applied to the conductor and the electrodes to start the electrolysis of the water to be treated; and a third treatment step of stopping the application of the potential to the conductor after an end of the second treatment step, and applying a positive potential to one of the pair of electrodes and applying a negative potential to the other of the electrodes in the presence of the water to be treated.

According to a third aspect of the present invention, there is provided an apparatus for water treatment comprising a pair of electrodes dipped in a running channel of water to be treated; a conductor dipped in the running channel of the water to be treated, the conductor being capable of collecting at least microbes; and a controller capable of controlling the application of potentials to each of the electrodes and the conductor, and capable of controlling the flow of the water to be treated. In this case, the controller executes a first treatment step of applying a positive potential to the conductor in a flow state of the water to be treated, and negative potentials to the electrodes to adsorb the microbes on the conductor, a second treatment step of stopping the flow of the water to be treated after an end of the first treatment step, and increasing the potentials applied to the conductor and the electrodes to start the electrolysis of the water to be treated while the polarities of the potentials applied to the conductor and the electrodes are maintained intact in the presence of the water to be treated, and a third treatment step of stopping the application of the potential to the conductor after an end of the second treatment step, and applying a positive potential to one of the pair of electrodes and applying a negative potential to the other of the electrodes in the presence of the water to be treated.

According to a fourth aspect of the present invention, there is provided an apparatus for water treatment comprising a pair of electrodes dipped in a running channel of water to be treated; a conductor dipped in the running channel of the water to be treated, the conductor being capable of collecting at least microbes; and a controller capable of controlling the application of potentials to each of the electrodes and the conductor, and capable of controlling the flow of the water to be treated. In this case, the controller executes a first treatment step of applying a positive potential to the conductor in a flow state of the water to be treated, and negative potentials to the electrodes to adsorb the microbes on the conductor, a second treatment step of stopping the flow of the water to be treated after an end of the first treatment step, reversing polarities applied to the conductor and the electrodes in the presence of the water to be treated, and increasing the potentials applied to the conductor and the electrodes to start the electrolysis of the water to be treated, and a third treatment step of stopping the application of the potential to the conductor after an end of the second treatment step, and applying a positive potential to one of the pair of electrodes and applying a negative potential to the other of the electrodes in the presence of the water to be treated.

The method or the apparatus for water treatment of the present invention further comprises a treatment step of discharging the water to be treated, in which the conductor and the electrodes are dipped, after an end of the third treatment step.

In the method or the apparatus for water treatment of the present invention, the conductor is a porous body.

In the method or the apparatus for water treatment of the present invention, the conductor is made of a carbon fiber.

In the method or the apparatus for water treatment of the present invention, the carbon fiber of the conductor includes precious metal added thereto, the precious metal being one selected from palladium, platinum, iridium, and tantalum.

In the method or the apparatus for water treatment of the present invention, in the third treatment step, chlorine and/or ozone is generated at one of the pair of electrodes, and active oxygen is generated at the other of the electrodes.

In the method or the apparatus for water treatment of the present invention, each of the electrodes includes precious metal added thereto, the precious metal being one selected from palladium, platinum, iridium, and tantalum.

According to a fifth aspect of the present invention, there is provided a hydroponic system for cultivating plants by supplying a nutrient liquid to a cultivation bed, comprising a path for recirculating a secondary nutrient liquid discharged from the cultivation bed to the same cultivation bed; and the foregoing water treatment apparatus provided in the path.

DESCRIPTION OF THE PREFERRED EMBODIMENTS

Figure 1:
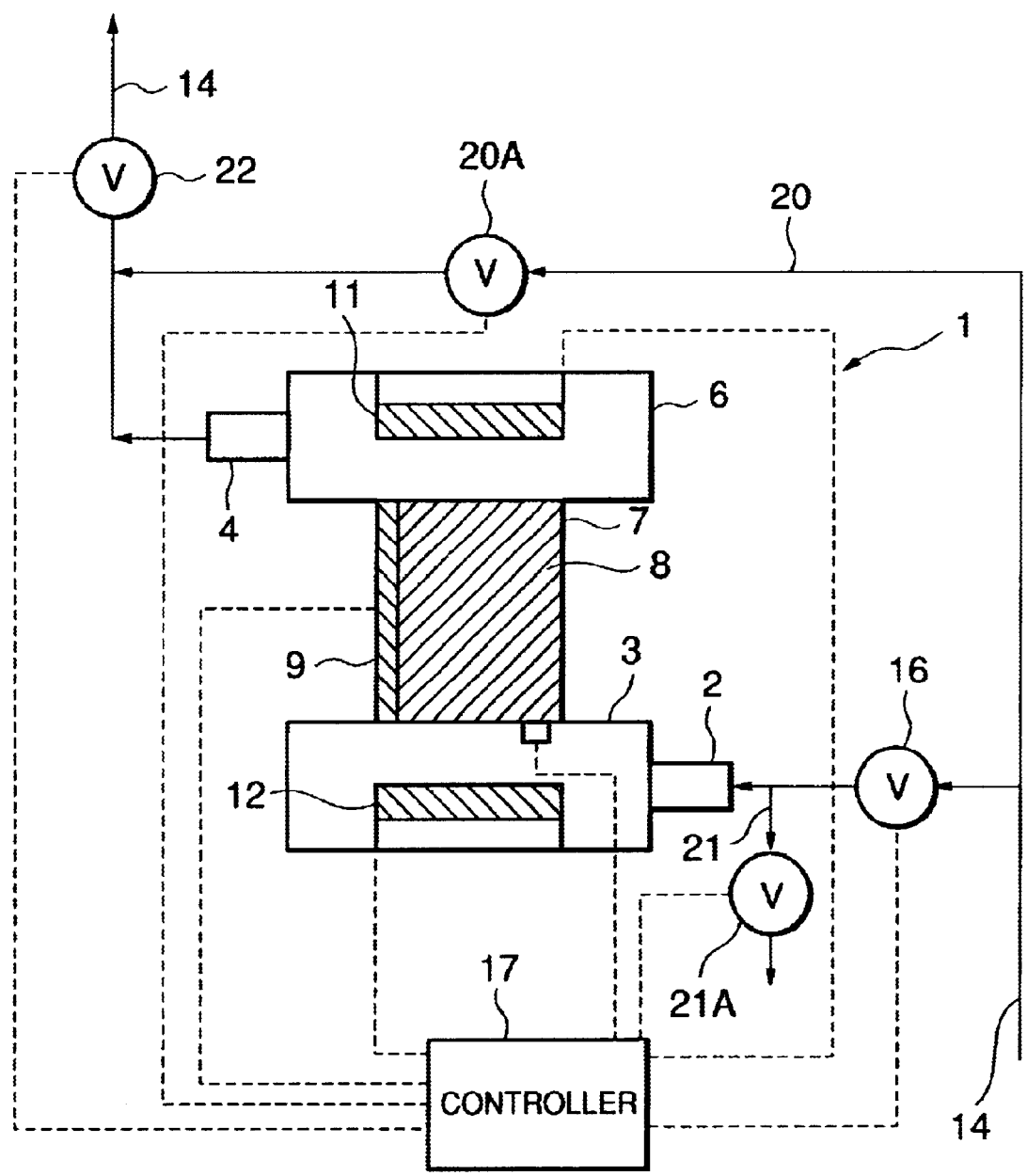
FIG. 1 is a block diagram showing a water treatment apparatus according to an embodiment of the present invention.

FIG. 1 is a block diagram showing an apparatus 1 for water treatment according to an embodiment of the present invention. This water treatment apparatus 1 comprises: an inlet side header 3 including an inlet 2 for introducing water to be treated, such as water for eating and drinking, stored in a reservoir, or water discharged from a hydroponic system; an outlet side header 6 including an outlet 4 for discharging the water to be treated; a housing portion 7 provided to communicate the headers 3 and 6 with each other; a carbon fiber 8 housed without any gaps in the housing portion 7; a current-carrying terminal 9 provided in the carbon fiber 8; an electrode 11 provided in the header 3 and disposed away from the carbon fiber 8; and an electrode 12 provided in the header 6 and disposed away from the carbon fiber 8.

The inlet 2 and the outlet 4 are connected into a water supply system 14 from a water pipe or the like from the reservoir. A valve 16 is provided in the water supply system 14 before the inlet 2. A running water valve 22 is connected to the water supply system 14 downstream of the outlet 4, and a bypass pipe 20 is connected to the water supply system 14. The bypass pipe 20 is connected to the upstream side of the valve 16 and between the outlet 4 and the running water valve 22. A bypass valve 20A is provided in the bypass pipe 20.

A drain pipe 21 including a drain valve 21A is connected between the inlet 2 and the valve 16, and the end part of this drain pipe 21 is communicated with a drain ditch (not shown). A reference numeral 17 denotes a controller provided to control the application of potentials to the current-carrying terminal 9 and the electrodes 11 and 12, and the opening/closing of the valve 16, the bypass valve 20A, the drain valve 21A, and the running water valve 22.

The carbon fiber 8 is a porous conductor, which serves as a filter for the water to be treated, disposed in the water treatment apparatus 1. Each of the current-carrying terminal 9, and the electrodes 11 and 12 (making a pair sandwiching the carbon fiber 8) contains precious metal added at least to its surface, the precious metal being one selected from palladium (Pd), platinum (Pt), iridium (Ir), tantalum (Ta), etc.

Next, description will be made of the operation of the controller 17 in the foregoing constitution. The water treatment apparatus 1 is connected, for example, into the water supply system 14 for water for eating and drinking as shown in FIG. 1. The controller 17 is composed of, for example, a general-purpose microcomputer, which sequentially executes the following first to fourth treatment steps in accordance with preset programs.

(1) First Treatment Step

The controller 17 first closes the bypass valve 20A and the drain valve 21A, and opens the valve 16 and the running water valve 22. Accordingly, water to be treated flows through the inlet 2 into the header 3 of the water treatment apparatus 1. After filling the header 3, the water to be treated reaches the carbon fiber 8, and then flows through the inside into the header 6. After filling the header 6, the water to be treated flows out through the outlet 4. Thus, the electrodes 11 and 12, and the carbon fiber 8 are dipped in the water to be treated. Microbes such as bacteria, mold or the like are captured in very small holes formed in the surface of the carbon fiber 8 during their passage through the same. Alternatively, the microbes are captured by affinity between the carbon fiber 8 and the microbes, or the filter function of the carbon fiber 8, and secured.

Figure 2:
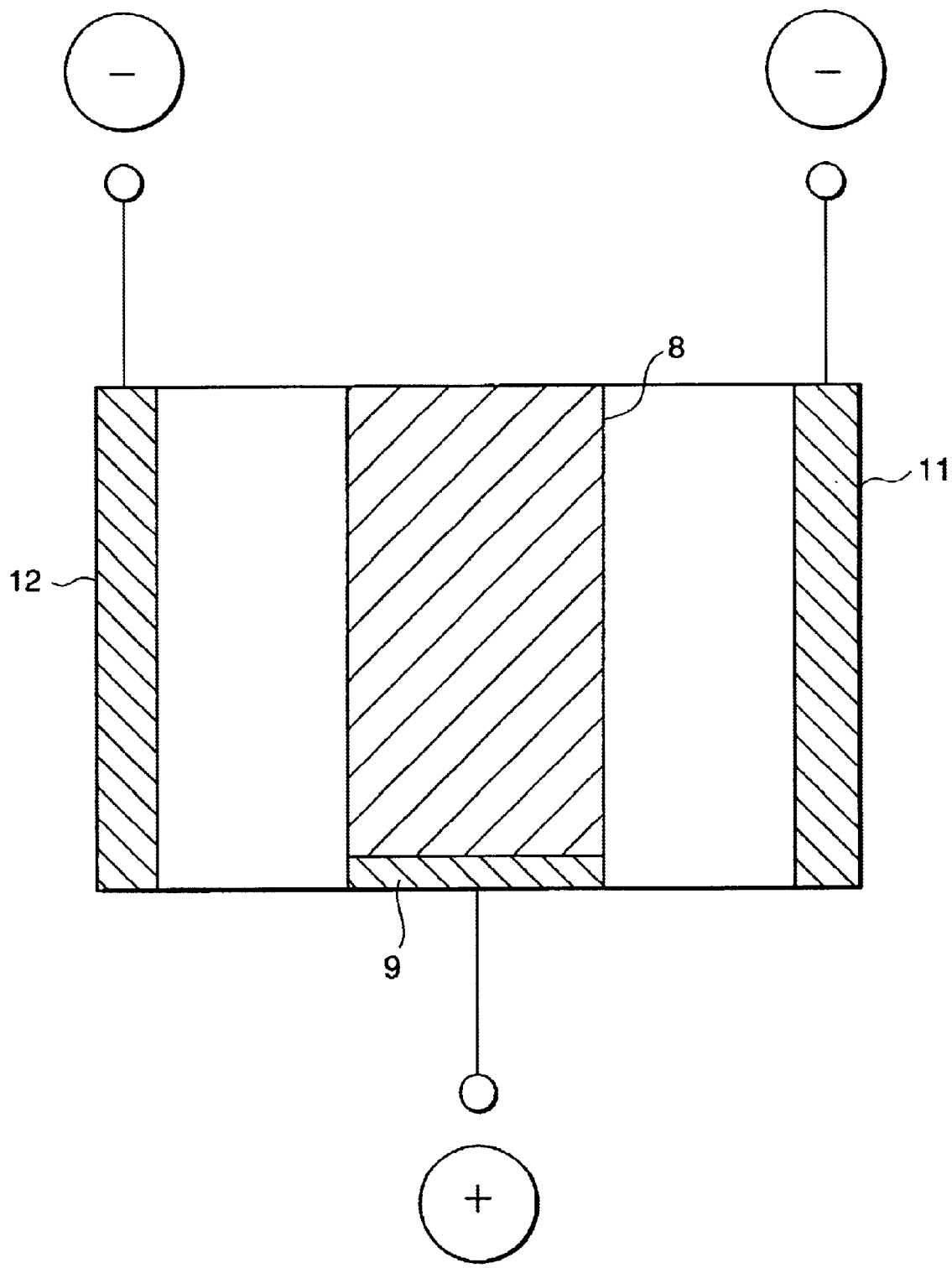
FIG. 2 is a view illustrating a state of potentials applied to a carbon fiber and each electrode in first and second treatment steps of the water treatment apparatus of FIG. 1.

On the other hand, as shown in FIG. 2, the controller 17 applies a positive potential (+) to the current-carrying terminal 9 of the carbon fiber 8, and negative potentials (−) to the electrodes 11 and 12. The potentials applied in this case are at levels not causing any water electrolysis, and decided according to the quality or the like of the water to be treated. In addition, it is assumed that the water to be treated fills portions between the electrodes 11 and 12 and the carbon fiber 8 in FIG. 2.

In the described case, being charged to negative potentials generally, the microbes are attracted to the carbon fiber 8 set at the positive potential. Accordingly, the microbes that have entered the carbon fiber 8 are attracted to the surface of the carbon fiber 8, and secured in the very small holes thereof smoothly and efficiently.

Through the execution of the foregoing first treatment step, the water to be treated, passed through the water treatment apparatus 1 and discharged through the outlet 4, becomes normal water for eating and drinking, from which the microbes have been secured to the carbon fiber 8 and removed. This first treatment step is executed during a period when it is necessary to supply water for eating and drinking (e.g., in the running water channel of the embodiment, during a period when a faucet is open to supply water. In the later-described reservoir, the treatment step is executed for a predetermined period).

Then, in the subsequent period of stopping the supplying of the water for eating and drinking (e.g., in the embodiment, during a period when the faucet is closed, or a period of time when the valve 16 and the running water valve 22 are closed by the controller 17), the controller 17 executes the second treatment step.

(2) Second Treatment Step

In the second treatment step, the controller 17 closes the valve 16 and the running water valve 22. Accordingly, the water to be treated stays in the headers 3 and 6 and the carbon fiber 8 of the water treatment apparatus 1. In this state, the controller 17 increases a potential applied to the current-carrying terminal 9 of the carbon terminal 8 to start the electrolysis of the water to be treated while maintaining intact the polarities of potentials applied to the current-carrying terminal 9 of the carbon fiber 8, and the electrodes 11 and 12. The potentials applied in this case are also decided according to the quality or the like of the water to be treated. It is also assumed that the water to be treated fills portions between the electrodes 11 and 12 and the carbon fiber 8 of FIG. 2.

By applying a positive potential to the carbon fiber 8 while the water to be treated stays in the headers 3 and 6 and the carbon fiber 8 of the water treatment apparatus 1, pH of the water to be treated is reduced in the vicinity of the surface of the carbon fiber 8, for example becoming an acid of about pH 2. In this case, since optimum pH of microbes is generally around pH 7, metabolic disorder occurs in the microbes in the water to be treated, deviated from the optimum pH, greatly reducing proliferation and heat resistance. Thus, since the microbes secured to the carbon fiber 8 are surrounded with acid water, a great reduction occurs in the heat resistance of the microbes, which normally has heat resistance up to +60° C. In other words, by starting the electrolysis of the water to be treated during the period of stopping the supplying of water for eating and drinking (e.g., in the embodiment, during a period when the faucet is closed), pH of the water to be treated is greatly deviated from the optimum pH of the microbes. In addition, since hypochlorous acid may be generated in the second treatment step, sterilization by this hypochlorous acid is carried out to a certain extent.

In the case of microbes such as protozoa, denaturation/dissolution of protein increases treatment efficiency. Accordingly, in the case of water to be treated, containing many such microbes, or if there are many positively charged microbes, the following second treatment step A is executed by reversing the potentials applied to the carbon fiber 8 and the electrodes 11 and 12 after the end of the first treatment step.

(3) Second Treatment Step A

Figure 3:
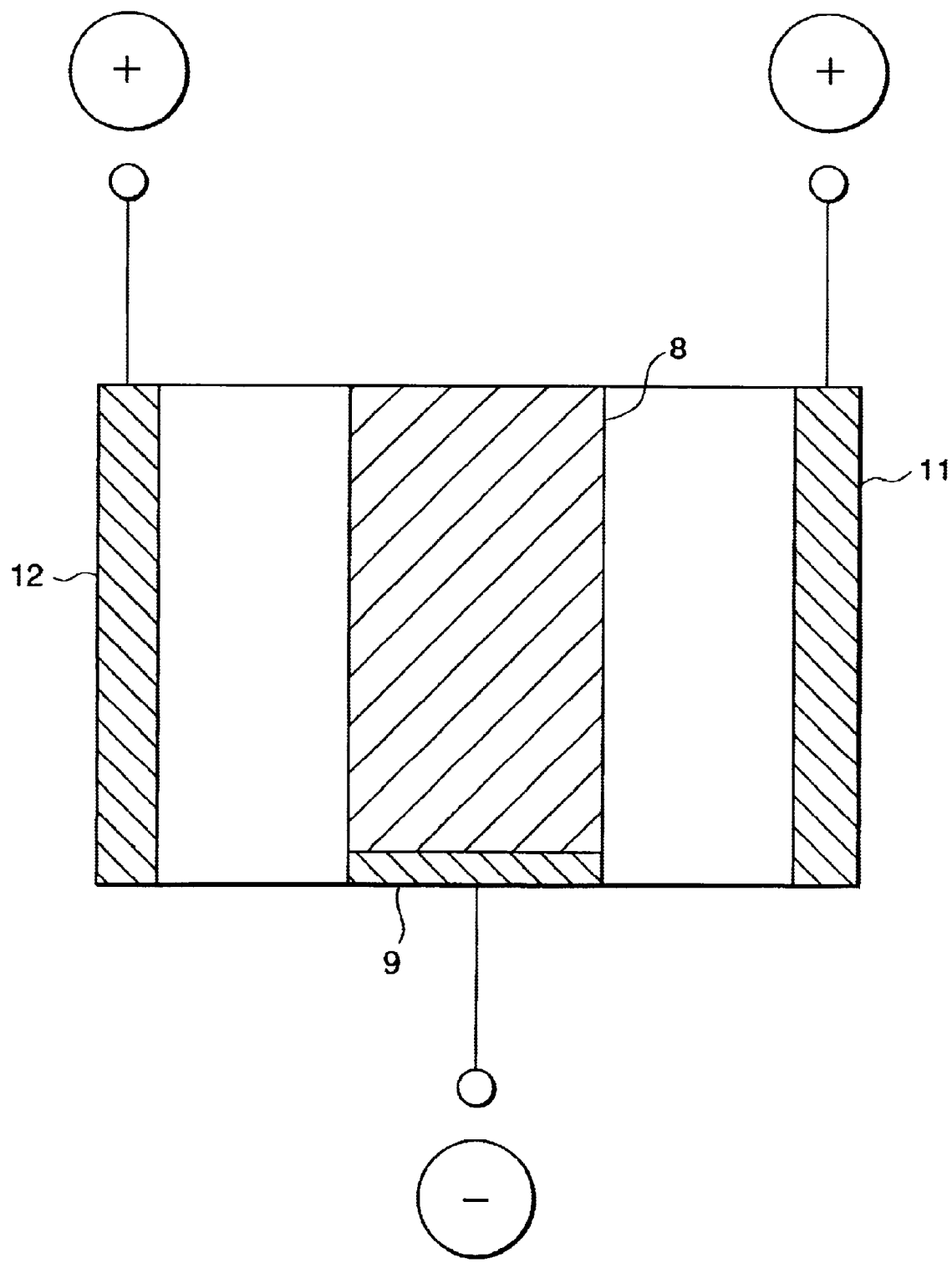
FIG. 3 is a view illustrating a state of potentials applied to a carbon fiber and each electrode in a second treatment step A of the water treatment apparatus of FIG. 1.

Specifically, in the second treatment step A, the controller 17 applies a negative potential (−) to the current-carrying terminal 9 of the carbon fiber 8, and positive potentials (+) to the electrodes 11 and 12 as shown in FIG. 3. The potentials applied in this case are also decided according to the quality or the like of the water to be treated. In addition, it is also assumed that the water to be treated fills portions between the electrodes 11 and 12 and the carbon fiber 8.

After the carbon fiber 8 is set at the negative potential, pH of the water to be treated is increased in the vicinity of the surface of the carbon fiber 8, for example becoming alkaline of about pH 11. Accordingly, since the microbes secured to the carbon fiber 8 is surrounded with alkaline water, protein of microbes such as protozoa is denatured/dissolved, reducing heat resistance thereof. Thus, in the second treatment step (including the second treatment step A, hereinafter), the effect of sterilization to be executed next is improved. Then, the controller 17 executes the third treatment step after carrying out the electrolysis of the water to be treated for a predetermined time.

(4) Third Treatment Step

Figure 4:
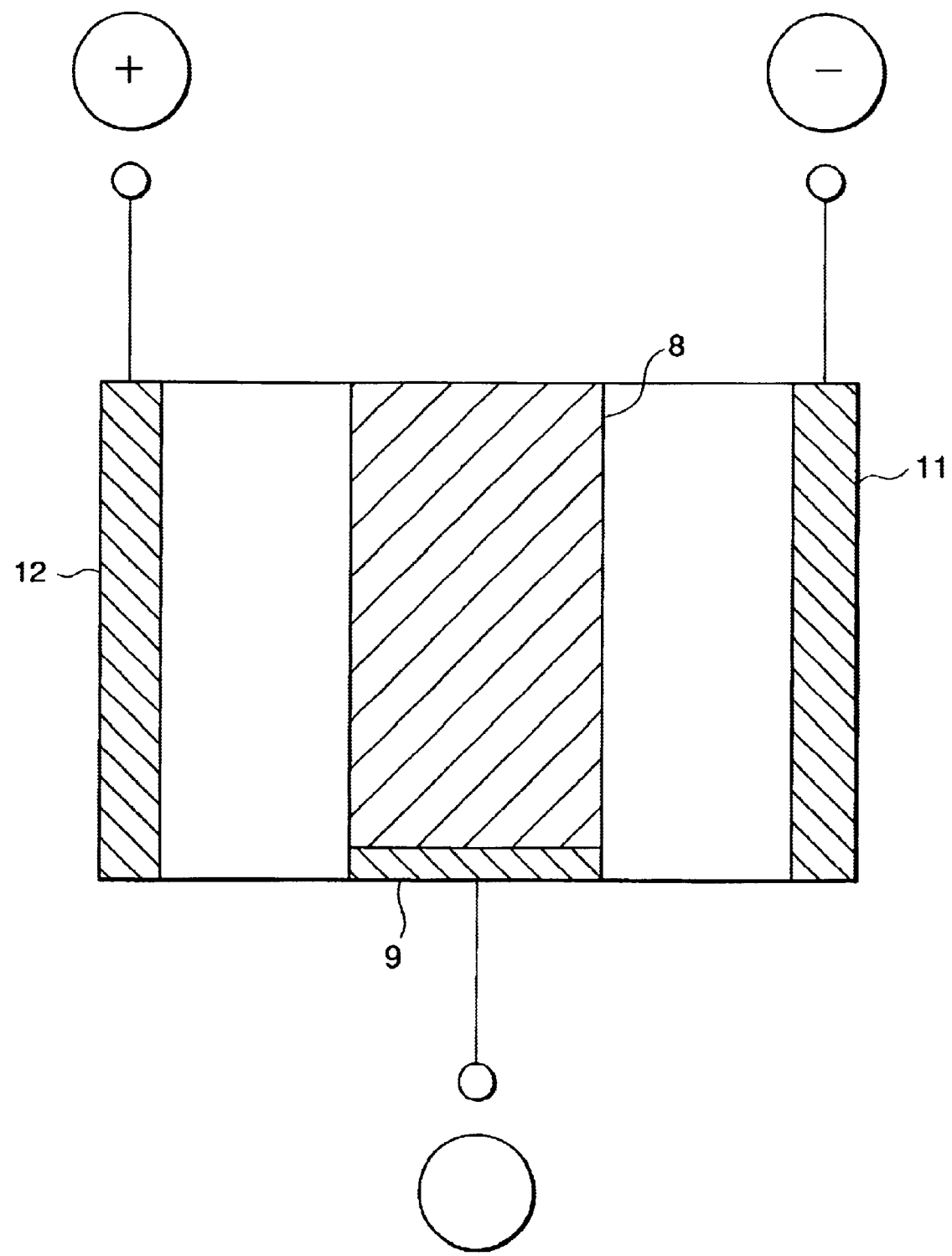
FIG. 4 is a view illustrating a state of potentials applied to a carbon fiber and each electrode in a third treatment step of the water treatment apparatus of FIG. 1.

In the third treatment step, as shown in FIG. 4, the controller 17 stops the application of the potential to the carbon fiber 8, and applies a positive potential to one of the electrodes 11 and 12, and applies a negative potential to the other (in this case, no positive or negative potentials are applied to the current-carrying terminal 9). Accordingly, currents flow to the water to be treated and the carbon fiber 8 between the electrodes 11 and 12 to generate heat from the carbon fiber and the water to be treated. At this time, the temperatures of the carbon fiber 8 and the water to be treated are increased at least to about +50° C. Because of the temperature increase caused by the generated heat, the microbes secured to the carbon fiber 8 in the first treatment step, and left and reduced for the heat resistance in the second treatment step are also killed efficiently in the third treatment step. Since the water to be treated is subjected to electrolysis to reduce/increase pH, even microbes that normally have heat resistance up to +60° C. can be killed at a low temperature of about +50° C.

In addition, the electrolysis of the water to be treated is started at each of the electrodes 11 and 12, and the electrode is set at a positive potential. In the electrode 12 as an anode electrode, chlorine ions contained in the water to be treated emit electrons to generate chlorine (or hypochlorous acid). Water molecules are also decomposed, and coupled with oxygen atoms to generate ozone. On the other hand, in the electrode 11 set at a negative potential to become a cathode electrode, active oxygen is generated. In the third treatment step, voltages applied to the electrodes 11 and 12 ma be DC or AC (commercial AC) voltages.

When an AC voltage is applied between the electrodes 11 and 12, or between the electrodes 11 and 12 and the carbon fiber 8, the nutrient liquid in both headers 3 and 6 and the housing portion 7 can be heated without causing any polarization on the electrodes. By the heating of the nutrient liquid in both headers 3 and 6, and the housing portion 7, the microbes having the heat resistance reduced by the electrolysis can be killed more efficiently. When a DC voltage is applied between the electrodes 11 and 12, or between the electrodes 11 and 12 and the carbon fiber 8, to generate heat, thus killing the microbes, with the DC voltage, water electrolysis occurs in addition to the foregoing ozone generation, and consequently energy is consumed for other than heat generation. However, since no water electrolysis occurs with the AV voltage, and the microbes can be killed by little consumption of power, energy can be greatly saved, providing an economic advantage. Moreover, since the AV voltage brings about mo chemical changes, the prolonged lives of the electrodes can be expected.

In this case, each of the electrodes 11 and 12 has precious metal added thereto, which is one selected from palladium, platinum, iridium, tantalum, etc. Thus, chlorine and/or ozone is actively generated at the electrode 11; and active oxygen at the electrode 11. Such chlorine (hypochlorous acid), ozone, and active oxygen can also kill the microbes on the surface of the carbon fiber 8 and in the water to be treated. Then, the controller 17 executes the fourth treatment step after the efficient killing of the microbes in the third treatment step.

(5) Fourth Treatment Step

In this fourth treatment step, the controller 17 opens the bypass valve 20A and the drain pipe 21A while the valve 16 and the running water valve 22 are closed, after the end of the third treatment step. Accordingly, the water to be treated from the water supply system 14 flows through the outlet 4 into the header 6, and passes through the housing portion 7 and the header 3, and then discharges from the drain pipe 21 to the drain ditch.

In this case, the microbes secured to the carbon fiber 8 from the direction of the inlet 2 are easily peeled off from the carbon fiber 8, and discharged through the drain pipe 21 to the drain ditch, by the water to be treated, which flows in from the direction of the outlet 4 and passes. Accordingly, since the carbon fiber 8 can be restored to be an original clean carbon fiber 8, which has no secured microbes, it is possible to maintain the carbon fiber 8 and the electrodes 11 and 12 neat and clean.

Thus, the microbes secured to the carbon fiber 8 are killed in the second and third treatment steps and, in the fourth treatment step, the water to be treated is supplied through the outlet 4 of the water treatment apparatus 1, and discharged through the drain pipe 21 connected between the inlet 2 and the valve 16. Accordingly, since the microbes killed and secured to the carbon fiber 8 can be peeled off, and washed away to the drain ditch, it is possible to achieve a good microbe securing operation by the carbon fiber 8 when a next first treatment step is executed.

Figure 6:
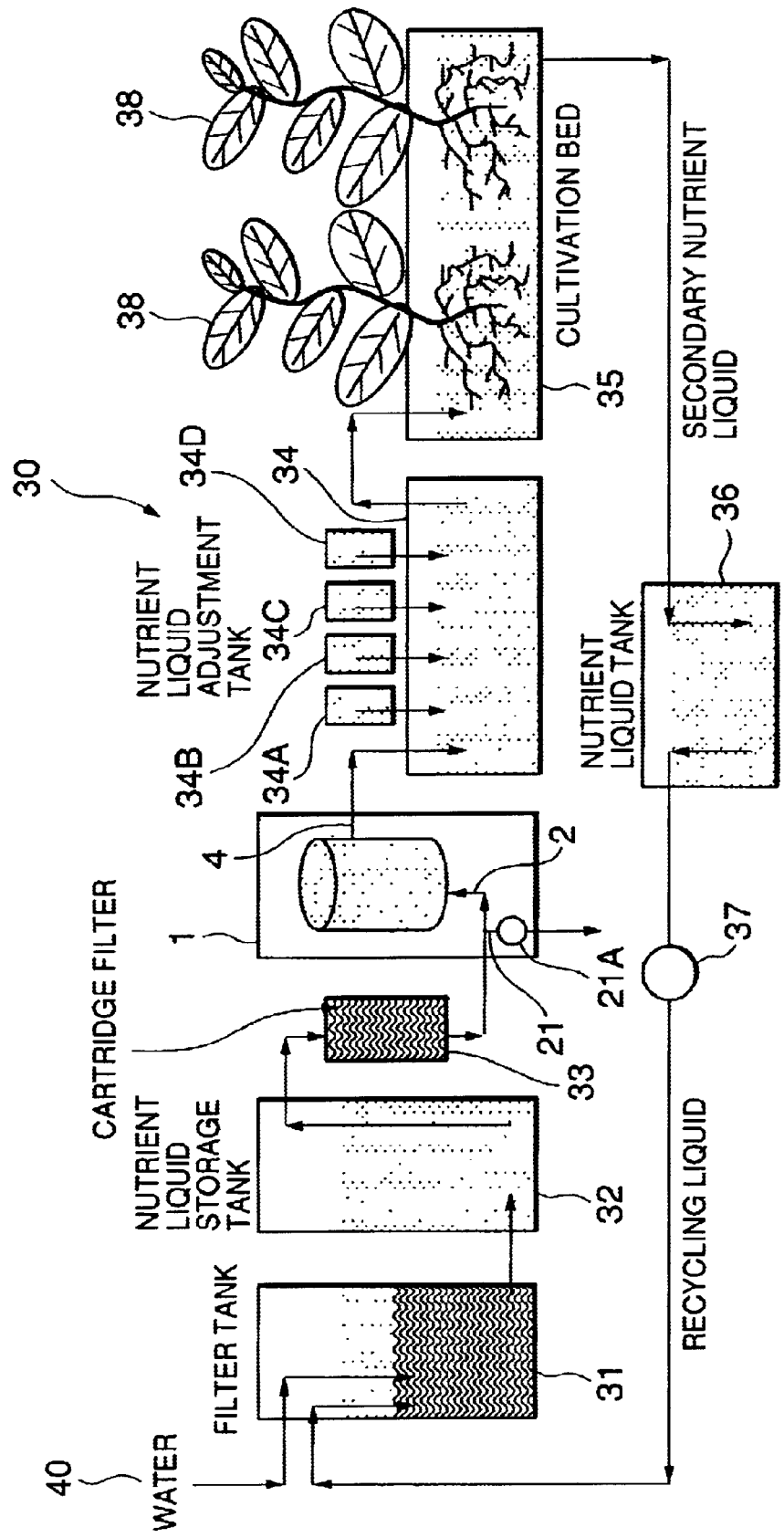
FIG. 6 is a view illustrating a hydroponic system, to which the water treatment apparatus of FIG. 1 is applied.

Now, description will be made of the example of employing the water treatment apparatus 1 of the present invention to a hydroponic system 30 by referring to FIG. 6. In FIG. 6, a secondary nutrient liquid (nutrient liquid with nutrition reduced because of its absorption by a plant in a cultivation bed 35) stored in a nutrient liquid tank 36 is sent out by a circulation pump 37. After the removal of refuse such as organic matters in a filter tank 31 using active carbon or the like, the secondary nutrient liquid flows into a nutrient liquid storage tank 32, and temporarily stored therein. The nutrient liquid stored in the nutrient liquid storage tank 32 flows into a cartridge filter 33 composed of a bobbin winder filter. After the refuse left without being removed at the filter tank 31, the nutrient liquid flows through the inlet 2 into the water treatment apparatus 1.

The nutrient liquid that has entered the water treatment apparatus 1 is subjected to electrolysis, resulting in the adsorption of fungi propagated in the nutrient liquid on the conductor (mainly carbon fiber 8), especially fusarium fungi or other bacteria (referred to as pathogenic fungi, hereinafter) that damages the root of a crop 38 as a plant in the cultivation bet 35. Thus, only the nutrient liquid having pathogenic fungi removed flow through the outlet 4 of the water treatment apparatus 1 into a nutrient liquid adjustment tank 34. For example, if the valve 16 and the running water valve 22 are closed one a day, and the second treatment step A (electrolysis) is carried out, the nutrient liquid becomes acid water of about pH 2, and the pathogenic fungi adsorbed on the conductor are deviated from the optimum pH, causing metabolic disorder. As a result, proliferation and heat resistance are greatly reduced.

Then, after the reductions made in the proliferation and heat resistance of the pathogenic fungi by the electrolysis of the nutrient liquid, the process proceeds to the third treatment step, where an commercial AC voltage is applied between the electrodes 11 and 12, or between the electrodes 11 and 12 and the carbon fiber 8. After the application of the commercial AC voltage, the nutrient liquid in both headers 3 and 6 and the housing portion 7 generates heat, thereby heating the pathogenic fungi. Accordingly, the pathogenic fungi that have suffered from metabolic disorder are killed.

After the end of the third treatment step, in the water treatment apparatus 1, the bypass valve 20A and the drain valve 21A are opened, and the pathogenic fungi that have been adsorbed on the conductor and killed are discharged through the drain pipe 21 to the drain ditch, and then the conductor is washed clean. A reference numeral 40 denotes water (in this case, tap water or underground water is used for water). The nutrient liquid circulated through the circulation path is absorbed by the crop 38, and reduced in amount by natural evaporation. Thus, the water treatment apparatus 1 is replenished with the water 40 by an amount equal to the reduced amount of the nutrient liquid.

Now, regarding the nutrient liquid adjustment tank 34, if there is a shortage of nutrients in the nutrient liquid in the cultivation bed 35 for the growth of the crop 38 planted in the cultivation bed 35, a nutrient that is short is selected from fertilizer and manure adjusting devices 34A, 34B, 34C and 34D (in this case, magnesium (Mg), iron (Fe), manganese (Mn), copper (Cu), and other fertilizer and manure (nutrients) expected to become short are separately housed in the fertilizer and manure adjusting devices 34A, 34B, 34C and 34D), and thrown into the nutrient liquid adjustment tank 34.

Thus, in the nutrient liquid adjustment tank 34, the nutrient liquid is adjusted to one containing a nutrient fit for the growth of the crop 38 planted in the cultivation bed 35. Then, the nutrient liquid adjusted to one containing the nutrient fit for the growth of the plant 38 flows from the nutrient liquid adjustment tank 34 into the cultivation bed 35 having the planted crop 38, and the predetermined amount of the nutrient liquid is absorbed by the crop 38. Subsequently, a secondary nutrient liquid obtained after the reduction of nutrition is discharged to return to the nutrient liquid tank 36, and sent out by the circulation pump 37 again. Accordingly, the nutrient liquid is repeatedly recycled as a recycling liquid.

Thus, since the water treatment apparatus 1 is provided in the path of recirculating the secondary nutrient liquid out of the cultivation bed 35 to the same, it is possible to heat the pathogenic fungi contained in the nutrient liquid circulated through the path for the flowing of the nutrient liquid and the secondary nutrient liquid by greatly deviating them from the optimum pH. Accordingly, by causing metabolic disorder in the pathogenic fungi present in the circulation path of the cultivation bed 35, it is possible to perform sterilization by heating and killing the pathogenic fungi suffering from the metabolic disorder. As a result, since the conventional necessity of a large amount of energy for the nutrient liquid heating and sterilization using the heater is eliminated, great energy conservation can be achieved.

In addition, since sterilization of the pathogenic fungi propagated in the nutrient liquid is carried out by using ozone or ultraviolet rays, it is possible to suppress reductions in the concentrations of iron, manganese, etc., contained in the nutrient liquid. Thus, iron or manganese deficiency of the crop 38 cultivated in the cultivation bed 35 can be prevented. Moreover, it is possible to prevent any adverse effects of the residue or accumulation of toxic materials on the crop 38 itself or men and cattle fed with the crop 38, which easily occur when conventional fungicide is used. As a result, the effect of removing pathogenic fungi in the circulation path can be greatly improved, making it possible to grow a clean and hygienic crop 38.

In the embodiment, the positive potential (+) was applied to the current-carrying terminal 9 of the carbon fiber 8, and the negative potentials (−) to both electrodes 11 and 12 in the second treatment step. In the second treatment step A, the negative potential (−) was applied to the current-carrying terminal 9 of the carbon fiber 8, and the positive potentials (+) to both electrodes 11 and 12. However, the process is not limited to such, and in the second treatment step, the second treatment step and the second treatment step A may be alternatively carried out. In other words, in the second treatment step, positive potentials (+) and negative potentials (−) may be alternately applied to the carbon fiber 8 and both electrodes 11 and 12 to kill acid or alkaline microbes of optimum pH. In this case, the present invention is similarly advantageous.

The water treatment apparatus 1 was provided in the running water channel such as a water pipe from the reservoir. However, there is no limitation in this regard. An advantage is similar even if the water treatment apparatus is directed set in the reservoir or provided in the running channel of discharged water. In the embodiment, the conductive carbon fiber was used as a conductor. There is no limitation in this regard, and fibers other than the carbon fiber 8 can be used as long as they are conductors capable of collecting microbes.

In addition, if precious metal such as palladium, platinum, iridium or tantalum is added to the surface of the carbon fiber 8, the deterioration of the carbon fiber itself can be suppressed to prolong its life, and to efficiently generate hypochlorous acid.

Figure 5:
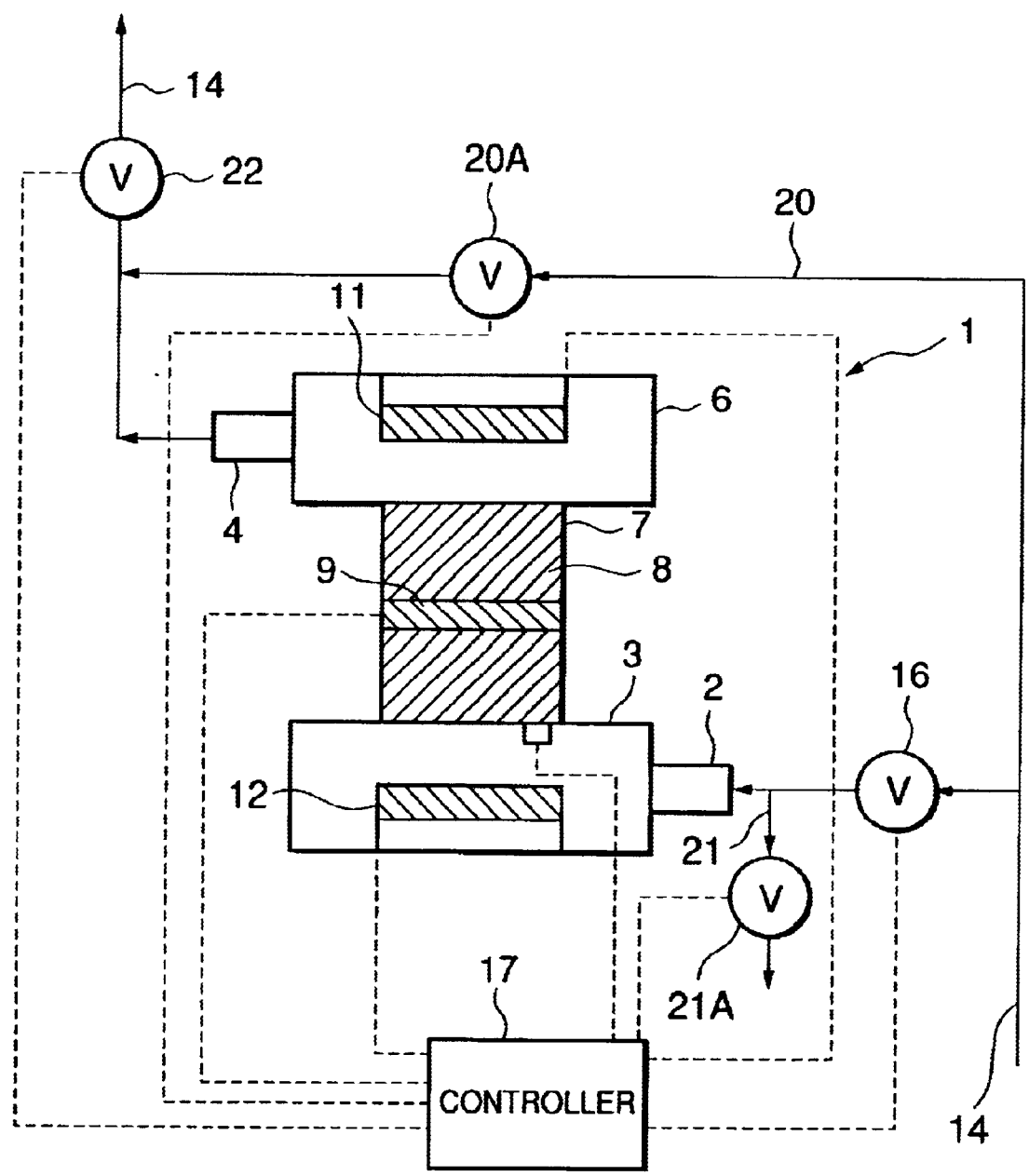
FIG. 5 is a block diagram showing a water treatment apparatus according to another embodiment of the present invention.

If the current-carrying terminal 9 is disposed roughly in the center of the carbon fiber 8 as shown in FIG. 5, the application of the potential to the carbon fiber 8 is made more uniform. In this case, however, it is necessary to mortgage water flowing by forming the current-carrying terminal 9 in a net shape, or providing a punching hole or the like. In this case, it is assumed that the current-carrying terminal 9 is made of a material similar to those of the electrodes 11 and 12.

The conductor was described as the conductive carbon fiber 8. However, the conductor may be composed of the current-carrying terminal 9, and a nonconductive filter member such as a porous fiber, cotton, a synthetic fiber or the like. In such a case, by applying a positive potential to the current-carrying terminal 9 of the water treatment apparatus 1 shown in FIG. 5, and negative potentials to both electrodes, the microbes can be attracted to the current-carrying terminal 9, and collected by the filter member. Thereafter, it is only necessary to sequentially carry out the second to fourth treatment steps.

For the microbes collected on the carbon fiber 8 and killed, the water to be treated was supplied through the outlet 4 of the water treatment apparatus 1, and then discharged through the drain pipe 21 connected between the inlet 2 and the valve 16. However, the carbon fiber 8 may be washed by supplying water to be treated through the inlet 2, and then discharging it through the outlet 4. In such a case, it is necessary to mortgage water flowing by forming the carbon fiber 8 in a net shape, setting the carbon fiber 8 at a negative potential by applying negative potentials to both electrodes, and supply the water to be treated through the inlet 2 after causing reaction with the microbes charged at the negative potential to peel the microbes off, or facilitating peeling-off.

Furthermore, the water treatment apparatus 1 of the present invention was provided between the cartridge filter 33 and the nutrient liquid adjustment tank 34 of the hydroponic system 30. However, there is no limitation in this regard, and the water treatment apparatus 1 may be provided anywhere in the circulation path for circulating the nutrient liquid and the secondary nutrient liquid. The water treatment apparatus 1 was provided in one place of the hydroponic system 30. However, there is no limitation in this regard, and the water treatment apparatus 1 may be provided in two or more places in the circulation path of the nutrient liquid and the secondary nutrient liquid.

As discussed above in detail, according to the present invention, first, the microbes contained in the water to be treated are collected by the conductor in the first treatment step. In this case, since the microbes have been charged at a negative potential, the microbes are attracted to the conductor charged at a positive potential. Thus, the securing of the microbes to the conductor is smoothly and efficiently carried out.

Then, in the second treatment step, the flow of the water to be treated is stopped, and potentials applied to the conductor and the electrodes are increased to start the electrolysis of the water to be treated while the polarities of the potentials applied to the conductor and the electrodes are maintained intact. Thus, pH of the water to be treated is increased in the vicinity of the surface of the conductor to become acid, making it possible to greatly deviate pH of the water to be treated around the microbes from the optimum pH of the microbes. In addition, hypochlorous acid is similarly generated in the surface of the conductor. Since the microbes are metabolized by oxygen, metabolic disorder occurs by the water to be treated, deviated from the optimum pH, greatly reducing proliferation and heat resistance. As a result, the microbes can be killed at a lower temperature increase. In this second treatment step, sterilization is carried out to a certain extent by the hypochlorous acid.

In the third treatment step, the application of the potential to the conductor is stopped, and a positive potential is applied to one of the pair of electrodes and a negative potential is applied to the other. Thus, the water to be treated generates heat. The temperature increase caused by such heat generation kills the microbes, which have been secured to the conductor and suffered from the metabolic disorder because of the deviation of the water to be treated from the optimum pH. By the above-described operation, according to the present invention, it is possible to greatly improve the effect of removing the microbes contained in the water to be treated by greatly deviating the water to be treated, such as water for eating and drinking, discharged water or the like, from the optimum pH so as to efficiently secure/kill the microbes at a low temperature increase.

Moreover, according to the present invention, first, the microbes contained in the water to be treated are collected by the conductor in the first treatment step. In this case, since the microbes have been charged at a negative potential, the microbes are attracted to the conductor charged at a positive potential. Thus, the securing of the microbes to the conductor is smoothly and efficiently carried out.

Then, in the second treatment step A, the flow of the water to be treated is stopped, the polarities of the potentials applied to the conductor and the electrodes are reversed, and potentials applied to the conductor and the electrodes are increased to start the electrolysis of the water to be treated. Thus, pH of the water to be treated is increased in the vicinity of the surface of the conductor to become alkaline, making it possible to greatly deviate pH of the water to be treated around the microbes from the optimum pH of the microbes. Since the microbes are metabolized by oxygen, metabolic disorder occurs by the water to be treated, deviated from the optimum pH, greatly reducing proliferation and heat resistance.

Then, third treatment step is executed. Specifically, the application of the potential to the conductor is stopped, and a positive potential is applied to one of the pair of electrodes and a negative potential is applied to the other. Thus, the water to be treated generates heat. The temperature increase caused by such heat generation kills the microbes, which have been secured to the conductor and suffered from the metabolic disorder because of the deviation of the water to be treated from the optimum pH. By the above-described operation, according to the present invention, it is possible to greatly improve the effect of removing the microbes contained in the water to be treated by efficiently securing/killing the microbes contained in the water to be treated, such as water for eating and drinking, discharged water or the like.

Moreover, according to the present invention, after the end of the third treatment step, the microbes that have been collected by conductor and killed can be washed away. In this case, since the water to be treated, in which the conductor and the electrodes have been dipped, is discharged, the microbes stuck to the conductor and the electrodes can be easily peeled off by the discharged treated water. As a result, it is possible to maintain the conductor and the electrodes neat and clean.

In addition to the above, according to the present invention, since the conductor is a porous body, it is possible to greatly improve the effect of collecting the microbes. According to the present invention, the conductor is made of a carbon fiber in addition, it is possible to greatly deviate pH of the water to be treated from the optimum pH of the microbes in the connecting effect of the microbes of the first treatment step and the electrolysis of the second treatment step.

Further, according to the present invention, the carbon fiber constituting the conductor in addition to the above includes the added precious metal, which is one selected from palladium, platinum, iridium and tantalum. Thus, it is possible to suppress the deterioration of the conductor as the carbon fiber to prolong its life.

Furthermore, according to the present invention, in the third treatment step, in addition to the above, chlorine and/or ozone is generated at one of the electrodes, and active oxygen at the other. Thus, it is also possible to kill the microbes in the conductor and the water to be treated by the chlorine and/or ozone generated by the electrolysis at one electrode, which becomes an anode electrode by the application of a positive potential, and the active oxygen generated by the electrolysis at the other electrode, which becomes a cathode electrode by the application of a negative potential in the third treatment step.

According to the present invention, in addition to the above, each of the electrodes includes the added precious metal, which is one selected from palladium, platinum, iridium, and tantalum. Thus, chlorine and/or ozone generated at one of the electrodes can further improve the generation efficiency of active oxygen at the other.

According to the present invention, plant cultivation is carried out by supplying the nutrient liquid to the cultivation bed, the path is provided to recirculate the secondary nutrient liquid out of the cultivation bed to the same, and the foregoing water treatment apparatus is provided in this path. Thus, it is possible to surely kill the pathogenic fungi by greatly deviating the optimum pH of the pathogenic fungi present in the recirculation path of the cultivation bed to cause metabolic disorder, and then heating the pathogenic fungi. Accordingly, a large amount of energy for, for example the conventional sterilization carried out by heating the nutrient liquid is made unnecessary. As a result, since the pathogenic fungi in the cultivation bed can be greatly reduced with less energy, it is possible to achieve great energy conservation.

Moreover, since the pathogenic fungi propagated in the nutrient liquid are not sterilized by using any fungicide or ultraviolet rays, which was carried out, for example in the conventional case, it is possible to suppress reductions in the concentrations of iron and manganese contained in the nutrient liquid, and improve the effect of removing the pathogenic fungi in the recirculation path. Thus, it is possible to prevent the iron or manganese deficiency of the plant cultivated in the cultivation plant, and any adverse effects on the plant itself or men and cattle fed with the plant by the residue or accumulation of toxic materials, which may occur when fungicide is used. As a result, the present invention enables a clean and hygienic plant to be grown.

What is claimed is:

1. A method for water treatment comprising:
  a first treatment step of dipping a pair of electrodes and a conductor capable of collecting at least microbes in a running channel of water to be treated, and applying a positive potential to the conductor and applying negative potentials to the electrodes to adsorb the microbes on the conductor;
  a second treatment step of stopping the flow of the water to be treated after an end of the first treatment step, and increasing the potentials applied to the conductor and the electrodes to start the electrolysis of the water to be treated while the polarities of the potentials applied to the conductor and the electrodes are maintained intact in the presence of the water to be treated; and
  a third treatment step of stopping the application of the potential to the conductor after an end of the second treatment step, and applying a positive potential to one of the pair of electrodes and applying a negative potential to the other of the electrodes in the presence of the water to be treated.

2. A method for water treatment comprising:

a first treatment step of dipping a pair of electrodes and a conductor capable of collecting at least microbes in a running channel of water to be treated, and applying a positive potential to the conductor and applying negative potentials to the electrodes to adsorb the microbes on the conductor;

a second treatment step of stopping the flow of the water to be treated after an end of the first treatment step, reversing the polarities of the potentials applied to the conductor and the electrodes in the presence of the water to be treated, and increasing the potentials applied to the conductor and the electrodes to start the electrolysis of the water to be treated; and a third treatment step of stopping the application of the potential to the conductor after an end of the second treatment step, and applying a positive potential to one of the pair of electrodes and applying a negative potential to the other of the electrodes in the presence of the water to be treated.

3. An apparatus for water treatment comprising:

a pair of electrodes dipped in a running channel of water to be treated;

a conductor dipped in the running channel of the water to be treated, the conductor being capable of collecting at least microbes; and a controller capable of controlling the application of potentials to each of the electrodes and the conductor, and capable of controlling the flow of the water to be treated.

wherein the controller executes a first treatment step of applying a positive potential to the conductor in a flow state of the water to be treated, and negative potentials to the electrodes to adsorb the microbes on the conductor, a second treatment step of stopping the flow of the water to be treated after an end of the first treatment step, and increasing the potentials applied to the conductor and the electrodes to start the electrolysis of the water to be treated while the polarities of the potentials applied to the conductor and the electrodes are maintained intact in the presence of the water to be treated, and a third treatment step of stopping the application off the potential to the conductor after an end of the second treatment step, and applying a positive potential to one of the pair of electrodes and applying a negative potential to the other of the electrodes in the presence of the water to be treated.

4. An apparatus for water treatment comprising:

a pair of electrodes dipped in a running channel of water to be treated;

a conductor dipped in the running channel of the water to be treated, the conductor being capable of collecting at least microbes; and a controller capable of controlling the application of potentials to each of the electrodes and the conductor, and capable of controlling the flow of the water to be treated.

wherein the controller executes a first treatment step of applying a positive potential to the conductor in a flow state of the water to be treated, and negative potentials to the electrodes to adsorb the microbes on the conductor, a second treatment step of stopping the flow of the water to be treated after an end of the first treatment step, reversing polarities applied to the conductor and the electrodes in the presence of the water to be treated, and increasing the potentials applied to the conductor and the electrodes to start the electrolysis of the water to be treated, and a third treatment step of stopping the application of the potential to the conductor after an end of the second treatment step, and applying a positive potential to one of the pair of electrodes and applying a negative potential to the other of the electrodes in the presence of the water to be treated.

5. A method or an apparatus for water treatment according to any one of claims 1 to 4, further comprising a treatment step of discharging the water to be treated, in which the conductor and the electrodes are dipped, after an end of the third treatment step.

6. A method or an apparatus for water treatment according to any one of claims 1 to 4, wherein the conductor is a porous body.

7. A method or an apparatus for water treatment according to any one of claims 1 to 4, wherein the conductor is made of a carbon fiber.

8. A method or an apparatus for water treatment according to claim 7, wherein the carbon fiber of the conductor includes precious metal added thereto, the precious metal being one selected from palladium, platinum, iridium, and tantalum.

9. A method or an apparatus for water treatment according to any one of claims 1 to 4, wherein in the third treatment step, chlorine and/or ozone is generated at one of the pair of electrodes, and active oxygen is generated at the other of the electrodes.

10. A method or an apparatus for water treatment according to any one of claims 1 to 4, wherein each of the electrodes includes precious metal added thereto, the precious metal being one selected from palladium, platinum, iridium, and tantalum.

11. A hydroponic system for cultivating plants by supplying a nutrient liquid to a cultivation bed, comprising:

a path for recirculating a secondary nutrient liquid discharged from the cultivation bed to the same cultivation bed; and a water treatment apparatus provided in the path, the water treatment apparatus being specified in claim 3 or 4.

* * * * *